United States Patent
Zhou et al.

(10) Patent No.: US 6,777,452 B2
(45) Date of Patent: Aug. 17, 2004

(54) PROMOTED SKELETAL IRON CATALYSTS FOR FISCHER-TROPSCH SYNTHESIS PROCESSES

(75) Inventors: Peizheng Zhou, Lawrenceville, NJ (US); Yijun Lu, Lawrenceville, NJ (US)

(73) Assignees: Hydrocarbon Technologies, Lawrenceville, NJ (US); Institue of Coal Chemistry, Taiyuan (CN)

(*) Notice: Subject to any disclaimer, the term of this patent is extended or adjusted under 35 U.S.C. 154(b) by 6 days.

(21) Appl. No.: 10/107,915

(22) Filed: Mar. 27, 2002

(65) Prior Publication Data

US 2002/0156137 A1 Oct. 24, 2002

Related U.S. Application Data

(63) Continuation-in-part of application No. 09/895,621, filed on Jul. 2, 2001, now abandoned, which is a continuation-in-part of application No. 09/399,852, filed on Sep. 21, 1999, now Pat. No. 6,277,895.

(51) Int. Cl.$^7$ .................. C07C 27/00; B01J 23/32; B01J 23/40; B01J 23/72
(52) U.S. Cl. ............... 518/713; 518/719; 518/721; 502/324; 502/327; 502/331
(58) Field of Search ................ 518/713, 719, 518/721; 502/324, 327, 331

(56) References Cited

U.S. PATENT DOCUMENTS

| | | | | |
|---|---|---|---|---|
| 4,503,162 A | * | 3/1985 | Windawi et al. | 502/174 |
| 4,521,394 A | * | 6/1985 | Windawi et al. | 423/363 |
| 4,604,375 A | * | 8/1986 | Soled et al. | 502/241 |
| 4,618,597 A | * | 10/1986 | Fiato et al. | 502/324 |
| 4,978,689 A | * | 12/1990 | Bell et al. | 518/709 |
| 4,994,428 A | * | 2/1991 | Bell et al. | 502/330 |
| 5,100,856 A | * | 3/1992 | Soled et al. | 502/329 |
| 6,265,451 B1 | * | 7/2001 | Zhou et al. | 518/700 |
| 6,277,895 B1 | * | 8/2001 | Zhou et al. | 518/715 |
| 6,319,872 B1 | * | 11/2001 | Manzer et al. | 502/66 |
| 6,602,922 B1 | * | 8/2003 | Davis et al. | 518/717 |
| 2002/0052423 A1 | * | 5/2002 | Zhou et al. | |
| 2003/0018086 A1 | * | 1/2003 | Price | |
| 2003/0109591 A1 | * | 6/2003 | Zhou et al. | |

* cited by examiner

*Primary Examiner*—Steven Bos
*Assistant Examiner*—William G Wright, Sr.
(74) *Attorney, Agent, or Firm*—Workman Nydegger

(57) ABSTRACT

Promoted skeletal iron catalysts are provided which contain 70–90 wt % iron together with promoters 0–5.0 wt. % copper, 0.1–10.0 wt. % manganese, and 0.1–3.0 wt. % potassium, with the balance being aluminum. The catalysts are prepared by mixing the metal chips or powders uniformly together, then melting and rapidly quenching the molten metals to form a solid metal alloy precursor including the promotor metals except potassium, removing most of the aluminum by caustic extraction/leaching to provide a base skeletal iron form, then loading the potassium promoter from a suitable potassium alcohol solution promoter. After evaporation of the solvent, the promoted skeletal iron catalyst is activated by contact with hydrogen. The promoted skeletal iron catalysts are utilized for F-T synthesis processes at 10–30 wt % catalyst concentration, 200–350° C. temperature, 1.0–3.0 Mpa pressure and gas hourly space velocity of 0.5–5.0 L/gcat-h to produce desired hydrocarbon liquid products. The promoted skeletal iron catalysts provide good catalytic activity and selectivity for hydrogen and CO conversions, for distillate fuel products are attrition resistant synthesis, and are readily separable from waxy liquid product by gravity sedimentation.

19 Claims, No Drawings

PROMOTED SKELETAL IRON CATALYSTS FOR FISCHER-TROPSCH SYNTHESIS PROCESSES

REFERENCE TO RELATED APPLICATIONS

This application is a continuation-in-part of U.S. patent application Ser. No. 09/895,621 filed Jul. 02, 2001, now abandoned, which is a continuation of Ser. No. 09/399,852, filed Sep. 21, 1999, now U.S. Pat. No. 6,277,895.

FIELD OF THE INVENTION

This invention pertains to promoted skeletal iron catalysts for use in Fischer-Tropsch synthesis processes for converting CO and $H_2$ in synthesis gas feeds to produce various desired hydrocarbon products. It pertains particularly to such promoted skeletal iron catalysts having specific metal compositions and which are prepared using improved method steps for providing improved performance including elevated middle-distillate yield, increased attrition resistance and catalyst settling rates for advantageous use in slurry-phase catalytic reactors.

BACKGROUND OF THE INVENTION

The Fischer-Tropsch (F-T) catalytic synthesis process is a well-known and effective route for converting synthesis gas feeds containing CO and $H_2$ into chemical feedstocks and hydrocarbon liquid fuels. Precipitated iron catalysts which have been under extensive development for such processes can achieve high catalytic activities, but break down easily to sub-micron particle size during reactor operations for production of hydrocarbon liquid fuels. Such particle breakdown results in difficulties for separating the very fine catalyst particles from the hydrocarbon liquid and waxy products, and has thus hindered commercialization of such F-T synthesis process. Some skeletal iron catalysts suitable for use in F-T synthesis reaction processes have been recently disclosed by U.S. Pat. Nos. 6,265,451 and 6,277,895 to Zhou et al. However, further improvements in such skeletal iron catalysts are desired.

The promoted skeletal iron catalysts of the present invention provide good potential for use in commercial F-T synthesis processes, particularly in slurry type reactors, because the catalyst has lower cost per unit mass of active metal, and has good resistance to particle attrition during vigorous hydrodynamic conditions existing in slurry phase reactors. Also, the used catalysts are readily separable from F-T waxy products by simple gravity sedimentation or by filtration of the catalyst.

SUMMARY OF THE INVENTION

This invention provides improved promoted skeletal iron catalysts containing mainly iron and promoted with minor amount of copper, manganese, and potassium. The promoted skeletal iron catalysts contain 50–90 wt % iron, 0–5.0 wt % copper, 0.1–5.0 wt % manganese, and 0.1–3.0 wt % potassium with the remainder being aluminum. The catalyst has good particle strength and provides high catalytic activity and selectivity towards the formation of desirable hydrocarbon products from the CO and $H_2$ feedstreams, particularly liquid transportation fuels. The promoted skeletal iron catalyst has catalytic activity comparable to that of precipitated iron catalyst, and more favorable product selectivity towards diesel fuel than that of either precipitated or fused iron catalysts, and can be used in either fixed bed catalytic reactors or slurry bed type reactors for Fischer-Tropsch synthesis processes for producing desired hydrocarbon products. The resulting hydrocarbon liquid products are also rich in alpha-olefins which are valuable feedstocks for chemicals production.

The promoted skeletal iron catalysts of this invention are prepared utilizing improved method steps, which include mixing together iron chips or powder with the non-ferrous metal chips or powders aluminum, copper and manganese, heating and melting the metal chips mixture to form a molten metal alloy, then rapidly cooling the molten metal alloy to room temperature (15–20° C.) such as by quenching in water, and then pulverizing the resulting solid metal alloy to provide fine precursor iron alloy particles having size range of 0.1–10 mm (10–10,000 microns). A major portion of the aluminum is removed by extracting/leaching by contacting with a suitable caustic solution such as NaOH or KOH to provide base iron catalyst particles. The base catalyst particles are next impregnated or loaded with the potassium promoter to provide 0.1–3.0 wt. % potassium. The skeletal iron catalyst is activated utilizing either high-temperature fixed-bed catalyst activation or in-situ activation method steps. The resulting promoted skeletal iron catalysts have high activity for catalyzing conversion of $H_2$ and CO contained in syngas feedstreams to produce various desirable hydrocarbon products, and are attrition resistant and do not breakdown easily to undesired submicron particle size during extended reaction operations. Because the spent catalyst particles have higher density and are readily separable from the hydrocarbon product liquids by gravity sedimentation, this skeletal iron catalyst is especially suitable for use in slurry-phase type reactors for Fischer Tropsch synthesis processes.

The promoted skeletal iron catalysts of this invention provide various advantages compared with conventional precipitated iron or fused iron catalysts, and also provide specific improvements over the known skeletal iron catalysts. These advantages includes simplified catalyst preparation methods utilizing large size metal chips for forming a molten metal alloy which is cooled rapidly to room temperature and pulverized to desired particle size range to provide a catalyst precursor material, and an improved method for loading the potassium promotor into the catalyst precursor. The catalyst can be effectively activated in either fixed-bed or in-situ reactors. These promoted skeletal iron catalysts provide good syngas conversion (CO conversion>80%) comparable to precipitated iron catalysts under industrial conditions, and have relatively stable activity and excellent selectivity for liquid transportation fuels and alpha-olefins, particularly in slurry-phase Fischer-Tropsch synthesis processes. Also, these catalysts provide good attrition resistance and sedimentation separation of used catalyst from liquid hydrocarbon slurries withdrawn from slurry-phase Fischer-Tropsch reactors.

DESCRIPTION OF INVENTION

The present invention provides improved promoted skeletal iron catalysts having unique composition for advantageous use in Fischer-Tropsch synthesis processes for CO and $H_2$ feedstreams for producing desired hydrocarbon liquid products. The promoted skeletal iron catalysts contain 70–90 wt % iron with the remainder being less than 10 wt % non-ferrous metal promoters of copper and manganese, and 0.1–3 wt % potassium, with the balance being aluminum. The promoted skeletal iron catalysts have surface areas in the range of 20–80 $m^2/g$, and preferably 30–65 $m^2/g$, and particle size range of 10–10,000 microns.

The catalyst preparation method steps for this invention includes first mixing iron chips/powder together uniformly with selected non-ferrous metal chips/powder, particularly aluminum, copper, and manganese in the proportion of 20–80 wt. % iron and 30–70 wt. % non-ferrous metals. A typical mixture may contain by weight 35–55% iron, 40–60% aluminum, 1–15% manganese and 0–10% copper. The metals uniform mixture is heated and melted to form a molten metal alloy, which is cooled rapidly to room temperature (15–20° C.) such as by quenching in water, and then pulverized to provide catalyst precursor particles having a 10–10,000 micron size range. The catalyst precursor particles are then extracted or leached by utilizing a suitable caustic solution such as 10–50% NaOH or KOH solution at 50–90° C. temperature for sufficient time such as 20–150 minutes to remove a major portion of aluminum from the iron alloy, and thereby form the base skeletal iron catalyst precursor material.

The resulting base skeletal iron catalyst precursor is next promoted with potassium by impregnating the potassium onto the base skeletal iron catalyst utilizing a suitable organic alcohol solution containing potassium, and then dried to evaporate the alcohol solvent and provide the promoted skeletal iron catalyst containing 0.1–3 wt. % potassium. Suitable alcohol solutions containing potassium may include but are not limited to methanolic potassium hydroxide, ethanolic potassium hydroxide, or potassium carbonate.

The dried promoted skeletal iron catalyst is next reduced and/or activated such as by utilizing a hydrogen flow of 0.05–1.0 NL/g-cat/h in a fixed-bed reactor at a temperature of 300–350° C. for 2–12 hours to provide an active promoted skeletal iron catalyst, which can be then mixed with a suitable reaction medium such as liquid paraffin or ethanol and transferred into a reactor for use in F-T synthesis processes. Alternatively, the promoted skeletal iron catalyst can be activated or reduced by mixing with a suitable reaction medium such as liquid paraffin to provide a slurry form, and then transferred directly into a slurry-phase F-T reactor and treated with hydrogen at a flow rate of 0.3–3.0 NL/g-cat/h and 300–350° C. temperature for 3–48 hours. The skeletal iron catalyst is then ready for effective use in catalytic F-T synthesis processes utilizing CO and $H_2$ feedstreams for producing desired hydrocarbon products.

The final promoted skeletal iron catalyst particle size can be within a 10–10,000 micron range, with the larger particle size range of 1000–10,000 micron being for use in fixed bed reactors, and the smaller particle size range being 20–200 micron for use in slurry-phase reactors.

1. Preparation of Catalyst Precursor Particles

Mix together uniformly chips/powders of iron and non-ferrous metals selected from aluminum, copper and manganese to provide an iron content of 35–55 wt. %, 40–60 wt % non-ferrous metals and 5–15 wt. % manganese in the form of a carbonate compound. Heat and melt the uniformly mixed metals chips/powders in a suitable furnace such as an electric arc induction furnace to provide a molten metal alloy, and cool the molten alloy rapidly to room temperature (15–20° C.) by quenching in a suitable liquid such as water. Then mechanically pulverize the resulting solid metal alloy to provide iron alloy catalyst precursor particles having particle size range of 10–10,000 micron.

2. Preparation of Base Skeletal Iron Catalyst

The skeletal iron catalysts are prepared from the iron alloy catalyst precursor particles under an inert gas blanket by the following procedure:

Add a sufficient volume of caustic NaOH or KOH solution (10–50% concentration) into a stirred container, heat the solution to a temperature of 30–95° C., add the iron alloy particles (10–10,000 micron size) into the caustic solution, maintain the reaction condition for 2–150 minutes after the iron alloy particle addition is complete, and extract and/or leach out a major portion of the aluminum from the iron alloy particles. Then wash the treated iron alloy particles with deionized water to pH=7, replace the water with water-free ethanol, and temporarily store the resulting base skeletal iron catalyst particles in ethanol.

3. Impregnation of Potassium Promoter on the Base Skeletal Iron Catalyst

The impregnation of potassium promotor onto the base skeletal iron catalyst from step 2 is performed as follows:

Prepare an alcohol solution containing a potassium compound such as a carbonate or nitrate having the desired potassium content based on the iron content in the catalyst, to provide a potassium to iron weight ratio of 0.5–3:100. Transfer the base catalyst particles with alcohol solution to an rotating evaporator, then pour the required potassium solution into the same evaporator vessel, and vaporize the alcohol under controlled conditions of 40–80° C. temperature and 100–500 mm Hg vacuum pressure.

4. Activation of Promoted Skeletal Iron Catalyst

The promoted skeletal iron catalyst particles, after drying under vacuum, can be activated in either of the following ways before being used in an F-T reactor.

The dry catalyst particles are transferred into a fixed-bed activation reactor for activation with hydrogen, and then transferred to a F-T reactor, under inert gas protection while being transferred, the catalyst is then activated under a stream of hydrogen (0.05–1.0 NL/g-cat/hr) at a temperature of 300–350° for 2–12 hours.

After drying the impregnated catalyst particles, add sufficient liquid reaction medium such as liquid paraffin into the vessel to form a slurry, which is then transferred directly into the F-T reactor for in-site activation using hydrogen (0.3–3.0 NL/g-cat/hr) at 300–350° for 3–48 hours.

Synthesis Process Utilizing Promoted Skeletal Iron Catalyst

The promoted skeletal iron catalysts of this invention are uniquely useful in catalytic processes for Fischer-Tropsch synthesis of CO and $H_2$ feedstreams, particularly in slurry-phase reactors, to produce desired hydrocarbon products. Useful reaction conditions are $H_2$/CO molar ratio of 0.5–5:1 in the feedstreams and 5–40 wt. % catalyst loading relative to a reaction medium such as liquid paraffin, catalyst particle size of 1–10 mm (1000–10,000 microns) for fixed-bed reactors and 20–200 microns for slurry-phase reactors, 200–350° C. reaction temperature, 1.0–3.0 MPa system pressure, and gas hourly space velocity of 0.5–5 L/g-cat/h. A desired hydrocarbon liquid product containing used fine catalyst particles is withdrawn, and the fine catalyst particles are substantially removed from the liquid by sedimentation settling of the particles.

The improved preparation methods for the promoted skeletal iron catalyst of this invention and its performance are further disclosed by the following examples, which should not be construed as limiting the scope of the invention.

EXAMPLE 1

1. Iron and aluminum chips are mixed uniformly together with a small amount of manganese carbonate ($MnCO_3$) in respective weight ratio of 39:59:2, and heated in an electric-arc induction furnace under argon gas protection with constant stirring to form a molten metal alloy. Then the molten iron-aluminum-manganese alloy is rapidly cooled to room temperature (15–20° C.) by quenching in water. The resulting solid metal alloy is mechanically pulverized to 0.1–3 mm (10–3,000 micron) particle size range to provide catalyst precursor particles.

2. Under hydrogen atmosphere, provide 25% concentration NaOH into a container and heat to 75° C. temperature, then add the catalyst precursor particles into the NaOH caustic solution. Maintain these reaction condition for 30 minutes and extract and/or leach out a major portion of the aluminum from the precursor iron alloy particles. Then wash the leached iron particles with deionized water to pH=7, displace water with water-free ethanol and temporarily store the resulting catalyst particles in ethanol.

3. Next prepare a methanol solution of potassium carbonate and mix the leached iron catalyst particles with sufficient potassium solution to provide a potassium to iron weight ratio in the catalyst of 2:100, and vaporize water and ethanol away under conditions of 200 mm Hg vacuum and 60° C. temperature to provide dry promoted skeletal iron catalyst particles.

4. Transfer the promoted skeletal iron catalyst particles into a fixed-bed reactor and treat with hydrogen gas flow of 0.7 L/g-cat/hr at 350° C. temperature for 8 hours to reduce and activate the catalyst. Then under high-purity nitrogen gas protection, transfer the activated skeletal iron catalyst into a slurry-phase reaction medium for activity evaluation. The slurry-phase Fischer-Tropsch reaction conditions used for catalyst activity evaluation in a $CO+H_2$ feedstream include catalyst particle size of 0.044–0.074 mm (44–74 micron), catalyst loading of 15 wt. %, relative to reaction medium 0.7:1 $H_2$/CO molar ratio, 270° C. temperature, and 2.5 MPa pressure. Activity evaluation results for the promoted skeletal iron catalyst compared with a known precipitated iron catalyst under similar reaction conditions are provided in Table 1 below.

TABLE 1

EVALUATION RESULTS OF PROMOTED SKELETAL IRON CATALYSTS

| Example No. | 1 | 2 | 3 | 4 | Precipitated Iron* |
|---|---|---|---|---|---|
| Reaction Conditions | | | | | |
| Temperature, ° C. | 270 | 270 | 270 | 270 | 260 |
| Space Vel., NL/gcat-h | 3.0 | 3.0 | 3.0 | 3.0 | 1.8 |
| $H_2$/CO, mole. | 0.70 | 0.87 | 0.96 | 0.96 | 0.68 |
| Conversion, % | | | | | |
| CO | 81.7 | 74.3 | 76.4 | 75.5 | 81.0 |
| $H_2$ | 63.8 | 52.9 | 49.7 | 44.2 | 74.3 |
| Conv'd $H_2$/CO, mole. | 0.54 | 0.61 | 0.62 | 0.56 | 0.73 |
| Products, wt. % | | | | | |
| $C_1$–$C_2$, g/gFe-h | 0.052 | 0.063 | 0.052 | 0.045 | 0.030 |
| $C_3$–$C_4$, g/gFe-h | 0.080 | 0.076 | 0.066 | 0.057 | 0.036 |
| $C_5$+, g/gFe/h | 0.320 | 0.270 | 0.238 | 0.215 | 0.424 |
| $C_1$+, g/gFe-h | 0.452 | 0.415 | 0.357 | 0.318 | 0.490 |
| $CO_2$ (Conv'd CO) | 0.47 | 0.44 | 0.45 | 0.50 | 0.47 |
| $C_5$+ Simul. Distil. | | | | | |
| <177° C. | 44 | 49 | 46 | 47 | |
| 177–220° C. | 17 | 15 | 15 | 13 | |
| 220–360° C. | 27 | 26 | 28 | 27 | |
| >360° C. | 12 | 10 | 10 | 13 | |

*D. B. Bukar, X. Lang, Ind. Eng. Chem. Res. 1999, Vol. 38, 3270–3275.

Based on these results it is noted that the catalytic activity of the promoted skeletal iron catalyst is comparable to that of a precipitated iron catalyst.

5. After the catalyst evaluation tests were completed, the resulting product slurry material containing used skeletal iron catalyst particles and product wax was subjected to a catalyst/wax separation test by gravity sedimentation for 15 minutes duration at various temperatures. The catalyst separation results are shown in Table 2 below.

TABLE 2

CATALYST/WAX SEPARATION BY GRAVITY SEDIMENTATION

| Catalyst Separation Method | Product Slurry Temperature, ° C. | Catalyst remaining in clear wax, wt. % |
|---|---|---|
| Simple Sedimentation | 130 | 0.132 |
| | 185 | 0.085 |
| | 205 | 0.069 |
| Sedimentation with Hexane Dilution (1:1 in volume) | 30 | 0.096 |

The Table 2 results show that after 15 minutes sedimentation time, increased settling of the used skeletal iron catalyst particles in the clear wax product occurs at successively increased temperatures. Also with 100 vol. % hexane dilution of the catalyst/wax product, significant used catalyst particle settling occurs at only 30° C. temperature.

Catalyst/wax sedimentation for the promoted skeletal iron catalyst particle was further compared with a sample of precipitated iron catalyst at the various slurry temperatures for 15 minutes duration. The comparative test results are shown in Table 3.

TABLE 3

CATALYST/WAX SEPARATION BY GRAVITY SEDIMENTATION

| | Promoted Skeletal Iron Catalyst | Precipitated Iron Catalyst |
|---|---|---|
| Catalyst in Product Slurry, wt % | 15 | 3.0 |
| | Solid Concentration after Settling and (Efficiency), wt % | Solid Concentration after Settling and (Efficiency), wt % |
| Catalyst/Wax Slurry Temp., ° C. | | |
| 130 | 0.132 (99.12) | 1.372 (54.3) |
| 185 | 0.085 (99.43) | 0.983 (68.7) |
| 205 | 0.069 (99.54) | 0.882 (70.7) |

Based on the above catalyst/wax separation results, it is noted that although the concentration of catalyst solids in clear wax product is decreased at increased slurry temperatures for both the skeletal iron and the precipitated iron catalysts, the solid settling efficiencies i.e. the percentage of solids settled from the liquid wax after sedimentation compared to the original concentration, are significantly higher for the skeletal iron catalyst material.

The used promoted skeletal iron catalyst particle size distribution after 100 hour and 500 hour reaction times was also compared with that of fresh catalyst, with results being shown in Table 4 below.

TABLE 4

CATALYST PARTICLE SIZE DISTRIBUTION (W %)

| Particle Size (Microns) | Fresh Catalyst | Example 1 (After 100 hr Reaction) | Example 2 (After 500 hr Reaction) | Precipitated Iron (after 500 hr. Reaction) |
|---|---|---|---|---|
| 44–74 | 100 | 89.0 | 24.7 | 40 |
| 2.5–44 | 0 | 9.8 | 70.0 | 48 |
| <2.5 | 0 | 1.2 | 5.3 | 12 |

Table 4 results show that after the 100 hour and 500 hour periods of slurry phase reactor operations, the fresh promoted skeletal iron catalyst having initial 44–74 micron particle size range breaks down to smaller particles mostly in 2.5–44 micron range which are still easy to separate from wax slurry. When compared with the precipitated iron catalyst after 500 hour operation, the promoted skeletal iron catalyst had a desired lesser percentage of particles smaller than 2.5 microns, which are most difficult to separate from wax.

EXAMPLE 2

1. Iron and aluminum chips are mixed uniformly together with small amounts of manganese carbonate ($MnCO_3$) and copper oxide in respective metal weight ratio of 38.5:58.5:2:1, and heated in an electric-arc induction furnace under argon gas protection and constant stirring to form a molten metal alloy. Then rapidly quench and cool the iron-aluminum-copper-manganese alloy in water to room temperature (15–20° C.) and mechanically pulverize the solid metal alloy to 0.1–3 mm particle size to provide catalyst precursor particles.

2. Method steps 2, 3, 4 were same as steps 2,3 and 4 in Example 1. Activity evaluation and catalyst/wax separation test results are shown in Table 1, 2 and 3 above.

EXAMPLE 3

Method steps 1 and 2 for mixing together metal chips/powder and extracting/leaching out aluminum were same as steps 1 and 2 in Example 1.

Method step 3 for loading potassium promotor onto the catalyst was same as step 3 in Example 1, except that after the potassium loading step, the dried promoted skeletal iron catalyst particles were mixed with liquid paraffin medium to form a catalyst-liquid slurry under inert gas protection.

The catalyst-liquid paraffin slurry from step 3 was transferred into an autoclave reactor for catalyst activity testing. Prior to the test, the promoted catalyst was activated for about 48 hours at 310° C. temperature and 1.0 NL/gcat/h of hydrogen flow. Then the reactor was switched to a $CO/H_2$ feedstream under Fischer-Tropsch reaction conditions providing particle size of 0.044–0.074 mm, catalyst loading of 15 wt. % of reaction medium, catalyst 0.96:1 $H_2$/CO molar ratio, 270° C. temperature, and 2.5 MPa pressure. Activity evaluation results are provided in Table 1 above.

EXAMPLE 4

1. Method step 1 for mixing iron and metal powders together same as step 1 in Example 1.

2. Method step 2 for extracting/leaching aluminum same as step 2 in Example 1.

3. Method step 3 for potassium loading same as step 3 in Example 3.

4. Method step 4 for activating the promoted skeletal iron catalyst same as in Example 3.

Evaluation results are provided in Table 1

Although this invention has been disclosed broadly and also identifies specific catalyst composition and preparation method steps, it will be understood that modifications and variations can be made within the scope of the invention as defined by the following claims.

We claim:

1. A particulate promoted skeletal iron catalyst having high catalytic activity and product selectivity, good attrition-resistance under hydrodynamic reaction conditions, and enhanced separation of used catalyst particles from reaction product slurry in Fischer-Tropsch (F-T) synthesis processes, the catalyst comprising 70–90 wt. % iron, 0.–50. wt. % copper, 0.1–5.0 wt. % manganese, and 0.1–3.0 wt % potassium, with the balance being aluminum; said iron, copper, manganese and aluminum comprising a metal alloy having a skeletal structure; said skeletal iron catalyst having a 20–80 $m^2$/gm surface area and 10–10,000 micron particle size.

2. The promoted skeletal iron catalyst of claim 1, wherein the catalyst comprises 84–88 wt. % iron, 8–10 wt % aluminum, 1–3 wt % maganese and 0.5–2 wt % potassium.

3. The promoted skeletal iron catalyst of claim 1, wherein the catalyst surface area is 25–65 $m^2$/g and the particle size range is 60–2000 microns.

4. A method for preparing a promoted skeletal iron catalyst for use in Fischer-Tropsch synthesis processes, comprising the steps of:

(a) mixing iron and aluminum chips or powders and copper chips or copper compound and a manganese compound together uniformly to provide a metal chips and/or powder mixture, then heating and melting said mixture under inert gas protection and forming a molten metal alloy;

(b) cooling said molten metal alloy to provide a precursor solid metal alloy;

(c) pulverizing said precursor solid metal alloy to provide catalyst precursor particles having particle size range of 0.1–10 mm (100–10,000 microns), said precursor particles containing 35–55 wt % iron, 40–60 wt % aluminum, 0–10 wt % copper and 1–15 wt % manganese;

(d) contacting said catalyst precursor particles with a caustic solution of 10–50% concentration, at 50–90° C. for 50–150 minutes so as to extract and/or leach out a major portion of the aluminum to provide base catalyst particles having a skeletal structure, and (e) impregnating said base catalyst particles with a potassium promotor solution, followed by removing solvent by evaporation to provide the promoted skeletal iron catalyst containing 0.1–3.0 wt. % potassium.

5. The skeletal iron catalyst preparation method of claim 4, wherein said precursor metal alloy contains 39 wt % iron, 59 wt % aluminum and 2 wt. % maganese.

6. The skeletal iron catalyst preparation method of claim 4, wherein said molten metal alloy is cooled in less than 10 seconds to room temperature (15–20° C.) by quenching in water.

7. The skeletal iron catalyst preparation method of claim 4, wherein said base catalyst particles are screened to a desired particle size range in an alcohol medium so as to prevent exposure of the catalyst particles to air.

8. The skeletal iron catalyst preparation method of claim 4, wherein the potassium promotor is impregnated onto said base skeletal iron catalyst particles by mixing the base skeletal iron catalyst particles with an organic potassium-containing alcohol solution selected from methanolic potassium hydroxide, ethanolic potassium hydroxide, or ethanolic potassium carbonate, and then removing the alcohol solvent by vaporizing the solvent and drying the catalyst particles, whereby the potassium promotor is impregnated onto said base skeletal iron catalyst.

9. The skeletal iron catalyst preparation method of claim 8, wherein evaporating the potassium promotor alcohol solvent occurs at 40–80° C. temperature and 100–500 mm Hg vacuum, and provides a potassium to catalyst mass ratio of 0.5–3:0:100.

10. The skeletal iron catalyst preparation method of claim 8, wherein said potassium promotor is conducted by using an organic alcohol solution of a potassium compound with a concentration of 0.1–0.5 N potassium for impregnating the potassium promoter on the base skeletal iron.

11. The skeletal iron catalyst preparation method of claim 4, including activating said promoted skeletal iron catalyst by fixed-bed activation in a fixed-bed reactor at hydrogen flow rate of 0.05–1.00 NL/g-cat/h and temperature of 300–350° C. for 2–12 hours, then mixing said catalyst with a liquid reaction medium to form a slurry which is transferred into a slurry-phase Fischer-Tropsch reactor.

12. The skeletal iron catalyst preparation method of claim 4, including activating said promoted skeletal iron catalyst by in-situ activation by mixing the catalyst with a suitable liquid reaction medium and forming a catalyst liquid slurry, then introducing said slurry into a Fischer-Tropsch reactor, and activating said catalyst in-situ at 300–350° C. with a hydrogen gas flow rate of 0.3–3.0 NL/g-cat/h for 3 to 48 hours.

13. The skeletal iron catalyst preparation method of claim 12, wherein said promoted skeletal iron catalyst is mixed with liquid paraffinic hydrocarbon and placed in a slurry Fischer-Tropsch reactor for in-situ activation.

14. A catalytic Fischer-Tropsch (F-T) synthesis process utilizing a promoted skeletal iron catalyst in a reactor for producing hydrocarbon liquid products, the process comprising:

(a) feeding $H_2$ and CO-containing synthesis gas having $H_2$/CO molar ratio of 0.5–5:1 into a reactor containing a suitable reaction medium and the promoted skeletal iron catalyst as defined by claim 1;

(b) maintaining said reactor at conditions of 200–350° C. temperature, 1.0–3.0 MPa pressure, and gas hourly space velocity of 0.5–5.0 NL/g-Fe/h; and (c) withdrawing from said reactor a hydrocarbon gas/vapor and hydrocarbon liquid product containing fine sized used catalyst particles.

15. The catalytic F-T synthesis process of claim 14, said promoted skeletal iron catalyst having a particle size of 1–10 mm (1,000–10,000 micron) and being utilized in a fixed-bed reactor.

16. The catalytic F-T synthesis process of claim 14, said skeletal iron catalyst having a particle size of 0.02–0.2 mm (20–200 micron) and being utilized in a slurry-phase reactor.

17. The catalytic F-T synthesis process of claim 14, wherein said skeletal iron catalyst has a concentration of 5–40 wt. % relative to said reaction medium.

18. The catalytic F-T slurry-phase synthesis process of claim 14, including withdrawing a hydrocarbon gas/vapor and a hydrocarbon liquid/slurry product containing spent skeletal iron catalyst particles, and separating the spent skeletal iron catalyst from the hydrocarbon liquid product by a sedimentation step.

19. A catalytic Fischer-Tropsch (F-T) synthesis process utilizing a promoted skeletal iron catalyst in a reactor for producing hydrocarbon liquid products, the process comprising:

(a) feeding $H_2$ and CO-containing synthesis gas having $H_2$/CO molar ratio of 0.5–5:1 into a slurry-phase reactor containing the promoted skeletal iron catalyst as defined by claim 2 and a liquid medium at catalyst loading of 5–40 wt. % relative to the liquid medium;

(b) maintaining said reactor at conditions of 200–350° C., 1.0–3.0 MPa pressure, and gas hourly space velocity of 0.5–5.0 NL/g-Fe/h; and (c) withdrawing from said reactor a hydrocarbon gas/vapor and hydrocarbon liquid product containing particles of said promoted skeletal iron catalyst, and separating the used skeletal iron catalyst from the hydrocarbon liquid product by a sedimentation step.

* * * * *